United States Patent [19]

Palti

[11] Patent Number: 5,700,998
[45] Date of Patent: Dec. 23, 1997

[54] DRUG CODING AND DELIVERY SYSTEM

[76] Inventor: Yoram Palti, 51 Ruth Street, Haifa 34404, Israel

[21] Appl. No.: 550,930

[22] Filed: Oct. 31, 1995

[51] Int. Cl.$^6$ .............................. G06F 17/00; G06K 7/10
[52] U.S. Cl. ...................... 235/375; 235/462; 235/494
[58] Field of Search .............................. 235/462, 467, 235/375, 464, 494; 156/69, 64; 40/360, 630, 638, 306

[56] References Cited

U.S. PATENT DOCUMENTS

| | | | |
|---|---|---|---|
| 3,165,871 | 1/1965 | Roth et al. | 53/358 |
| 3,618,764 | 11/1971 | Bawdunlak | 209/111.6 |
| 3,807,128 | 4/1974 | Bauer | 53/482 |
| 3,834,525 | 9/1974 | Morgese et al. | 206/161 |
| 3,866,386 | 2/1975 | Granz | 53/398 |
| 3,890,763 | 6/1975 | Ullman | 53/442 |
| 4,034,035 | 7/1977 | Schwartz et al. | 264/77 |
| 4,036,362 | 7/1977 | Ullman | 53/482 |
| 4,258,533 | 3/1981 | Aka et al. | 53/557 |
| 4,365,456 | 12/1982 | Ullman | 53/69 |
| 4,449,042 | 5/1984 | Hampson et al. | 235/464 |
| 4,475,653 | 10/1984 | Ullman | 206/497 |
| 4,478,658 | 10/1984 | Wittner | 156/69 |
| 4,548,825 | 10/1985 | Vosg et al. | 426/383 |
| 4,587,407 | 5/1986 | Ahmed et al. | 235/467 |
| 4,642,967 | 2/1987 | Culpepper | 53/398 |
| 4,756,139 | 7/1988 | Le Bras | 53/398 |
| 4,807,428 | 2/1989 | Boisseau | 53/563 |
| 4,857,713 | 8/1989 | Brown | 235/375 |
| 4,870,802 | 10/1989 | Cerf | 53/563 |
| 4,962,625 | 10/1990 | Johnson et al. | 53/157 |
| 4,972,657 | 11/1990 | McKee | 53/411 |
| 4,982,552 | 1/1991 | Odenthal | 53/207 |
| 5,022,526 | 6/1991 | Crom | 206/459 |
| 5,118,369 | 6/1992 | Shamir | 156/64 |
| 5,238,240 | 8/1993 | Prim et al. | 271/299 |
| 5,376,771 | 12/1994 | Roy | 219/121.71 |
| 5,401,059 | 3/1995 | Ferrario | 283/67 |
| 5,457,895 | 10/1995 | Thompson et al. | 34/296 |

FOREIGN PATENT DOCUMENTS

| | | |
|---|---|---|
| A-59129/94 | 10/1994 | Australia . |
| 7-287736 | 1/1995 | Japan . |
| 8-7058 | 1/1996 | Japan . |
| 8-712 | 1/1996 | Japan . |

*Primary Examiner*—Donald T. Hajec
*Assistant Examiner*—Thien Minh Le
*Attorney, Agent, or Firm*—David M. Klein; Bryan Cave LLP

[57] ABSTRACT

A method of coding drug pills in which a machine readable code is placed on the outer surface of the drug pills. The code includes the name and dosage of the pill. The code is a linear bar code, a radial bar code, a code on the outer peripheral edge of a tablet, or a coaxial code extending completely around a capsule. The code is applied to the pill by a) engraving the outer surface of the pill, b) by applying a code label, or c) by painting the code on the pill. In a method of distributing coded drug pills, the identification information is read from the pill. A desired drug delivery information file for a patient is also read. The identification information for the drug pill is compared to the desired drug delivery information prior to delivery of the pill to the patient. An alarm is generated upon detection of discrepancies between the pill identification information and the desired drug delivery information. A drug delivery system includes: a code reader for reading identification information from individually coded drugs and from patients; an input device for retrieving the desired drug delivery information; a comparator for comparing the identification information for an individually coded drug with the desired drug delivery information for the patient; and an alarm signal that is initiated upon detecting a discrepancy between the identification information for a drug to be delivered to a patient and the desired drug delivery information.

5 Claims, 6 Drawing Sheets

DRUG CODING AND DELIVERY SYSTEM

BACKGROUND OF THE INVENTION

1. Field of the Invention

The present invention relates to a system for minimizing the occurrence of errors in drug delivery in hospitals and other medical facilities, and more particularly to a method of coding individual drugs to be administered to patients. The invention also relates to a method of and apparatus for reducing errors in the drug delivery procedure by identifying each patient and the drugs being administered to the patient, and by comparing these with predetermined drug delivery instructions for the patient.

2. Description of the Related Art

It is well known that there are serious problems in drug delivery to patients in medical institutions. It is generally estimated that up to 10% of the drugs given to hospitalized patients are in error. In a recent survey, it was found, for example, that just under 50% of the errors can be traced to the physician, while the remaining 50% can be traced to other errors in distribution and delivery. These errors not only endanger patients' lives, but may be fatal. At the very least, such errors interfere with their treatment and recovery.

The following is a typical drug delivery procedure in a hospital:

1. The attending physician prescribes a drug or drugs to a patient. This prescription may be inputted directly into the patient's record on the hospital's computer system, may be in a written document, or may be given orally to an attending nurse, etc.

2. The prescription is translated into an instruction to administer the prescribed drug in the patient's file, whether the file is on paper, on a stand-alone computer, or on a central computer system.

3. Usually, at predetermined times, a nurse in each ward, or an operator at a central facility prepares the drug delivery. The nurse or pharmacy operator collects the prescriptions relevant to the patients under their control, obtains the required drugs and prepares the drugs to be delivered to each patient in a separate special container. If the drug collection was done at a central facility, the prepared drugs are transferred to the patient ward and usually an attending nurse distributes them.

4. The actual delivery of the drugs or medications to the patients is done by a local nurse or other medical staff person that goes from patient to patient, identifies the patient and delivers the medication or the appropriate container with the medication.

5. Alternatively, the drug delivery may be done on a per patient basis. In this technique, the delivery person collects, from a portable drug storage cart, the drugs prescribed to each patient and delivers the drugs directly to the patient.

Errors may occur at each stage of the drug delivery procedure. In general, errors may result from an erroneous prescription by the physician or by errors in the drug delivery system. With respect to errors in the delivery chain, these generally result in two different ways: Erroneous selection of the prescribed drug i.e. misreading of a drug label, or delivery of a drug prescribed to one patient, to another patient. The latter error may result, for example, from non-recognition of a patient, or by a confused patient answering to the wrong name. Another type of error results from failure of the drug delivery person to give a patient prescribed drugs at the prescribed time because the patient is not near their bed or is not otherwise available.

Computerized hospital systems improve the drug delivery procedure by, for example, outputting lists of drugs to be given to each patient, and warning of improper prescriptions, e.g., due to allergies, drug interactions, and overdosing, etc. Nonetheless, these systems cannot prevent the errors that occur in the delivery of the drugs.

Each commercially available drug in the US has an identification number, the National Drug Code (NDC), which usually consists of ten digits. Drug packages and containers are usually marked by bar codes which contain the identification number, and may contain information regarding the weight of the tablet and other information. However, there is no universal code that is used to identify all drugs. Among the codes in use are the UPC (Universal Product Code), the often used code in medicine, the CODBAR, and the more comprehensive code developed by the Health Care Bar Code Council, CODE-39. Whatever the code that is used, since the codes are imprinted only on the drug packaging, once the drug is removed from it package, its identification is lost.

It would be desirable to have a system that minimizes errors in drug delivery. Toward this end, it would be desirable to have a drug delivery system that recognizes both the patients and the drugs, and matches them in accordance with the prescriptions, and can also warn to warn of improper prescriptions.

SUMMARY OF THE INVENTION

The present invention is a method of coding drugs to be administered to patients, and a method of and apparatus for reducing errors in the drug delivery procedure by identifying each patient and the drugs being administered to the patient, and by comparing these with predetermined drug delivery instructions for the patient.

In a method of coding drug pills, a machine readable code is placed on the outer surface of the pill. The code includes identification information for the pill, such as the name and dosage of the pill. The machine readable code is preferably a miniaturized on non-miniaturized linear bar code, or a radial bar code.

In one embodiment of the invention, the drug pill is a tablet and the machine readable code is located on an outer peripheral edge of the tablet. In a further embodiment, the drug pill is a capsule and the machine readable code comprises coaxial code means extending completely around the capsule.

The machine readable code is preferably applied to the pill by a) engraving the outer surface of the pill, b) by applying a code label to the outer surface of the pill, or c) by painting the code on the outer surface of the pill.

In a method of distributing the coded drug pills, the identification information is read from the pill prior to delivery of the pill to a patient. In order to prevent errors in drug delivery, desired drug delivery information for a patient may be read from a drug delivery information file prior to delivery of a pill to the patient. The identification information for the drug pill is then compared to the desired drug delivery information prior to delivery of the pill to the patient. An alarm is generated upon detection of discrepancies between the pill identification information and the desired drug delivery information.

A drug delivery system according to the invention includes:

a code reader for reading identification information from individually coded drugs and for reading identification information on patients to whom drugs are to be delivered;

means for retrieving desired drug delivery information for a patient to whom a drug is to be delivered;

means for comparing the identification information for an individually coded drug to be delivered to a patient with the desired drug delivery information for the patient; and means for generating an alarm upon detecting a discrepancy between the identification information for a drug to be delivered to a patient and the desired drug delivery information for the patient.

The drug delivery system according to the invention is preferably portable so that it may be moved from patient to patient during the drug delivery procedure.

DETAILED DESCRIPTION OF THE INVENTION

The present invention is a method of coding drugs and a method of and apparatus for dispensing coded drugs to prevent errors in drug delivery. Drugs and other medications to be delivered to patients are individually coded using an appropriate coding system. The apparatus for dispensing the coded drugs includes a code reader appropriate for the coding used on the drugs, and a control system for ensuring that a patient receives the correct medications and dosages, and for monitoring the drug delivery procedure to prevent errors.

Medication Coding

Each drug or medication that is delivered to a patient contains a unique identifier, and is identified as it is being distributed to that patient. As used herein, pill, capsule, medication, or drug may be used interchangeably, and may refer to a tablet, capsule, or any other type of drug or medication provided that the drug may be coded in accordance with the invention. In addition, it will be appreciated by those skilled in the art that the present drug delivery system and method may be used with medications other than prescription or other drugs, e.g., ampules and other containers of fluid drugs, fluid infusions, blood transfusions, other fluids, pastes, creams, foods, and even medical procedures such as X-rays, etc.

Identification of each drug is made by means of a code, such as a bar code, that is registered or imprinted on the medication or medication container. In cases where medication is delivered to a patient individually wrapped, whether in foil, paper, or other wrapper, any of the bar codes discussed herein may be applied to the wrapping. In the case of drugs dispensed as liquids, when the drug is poured from a storage container, e.g., a large bottle of the drug, to a smaller container which is to be delivered to the patient, a bar code may be attached to the small container so that the drug delivery to the patient may be recorded as discussed in further detail below.

Figure 1:
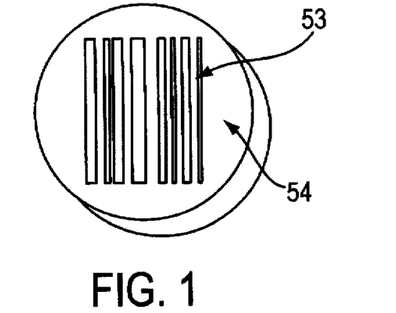
FIG. 1 is a schematic representation of a bar code printed on the surface of a disk-like tablet or that is contained on a patch or label that is adhered onto the surface of the tablet.
Figure 2:
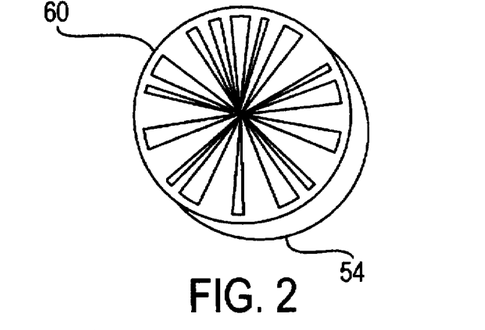
FIG. 2 is a schematic representation of a radial bar code printed on the surface of a disk-like tablet or that is contained on a patch or label that is adhered onto the surface of the tablet.
Figure 3:
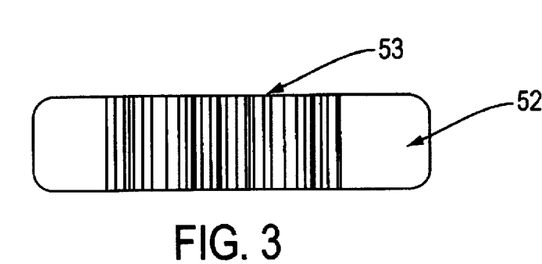
FIG. 3 is a schematic representation of a bar code printed on the surface of a capsule or other elongated medication, or that is contained on a patch or label that is adhered onto the surface of the capsule.
Figure 4:
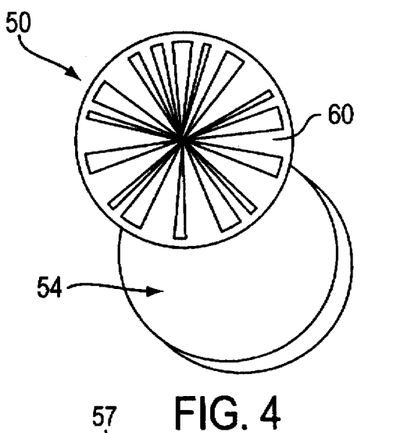
FIG. 4 is a schematic representation of a bar code printed on a patch or label that is to be adhered on medication that is dispensed as a disc-like tablet.
Figures 6, 7:
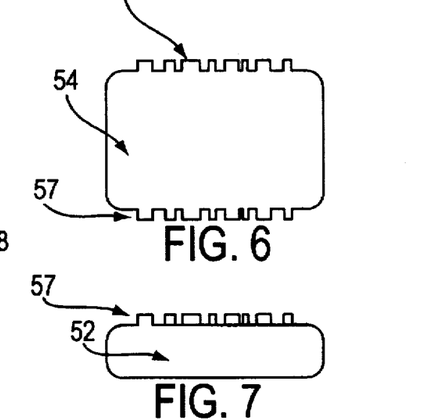
FIG. 6 is a schematic representation of a side view of a tablet with bars engraved onto its two flat surfaces.
FIG. 7 is a schematic representation of a side view of a cylinder-like capsule with bars engraved onto its upper surface.
Figure 8:
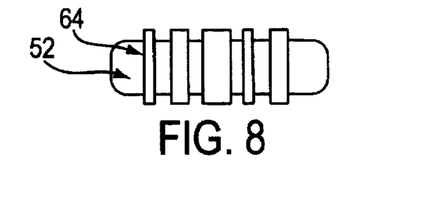
FIG. 8 is a schematic representation of a side view of a bar code engraved coaxially on the surface of a cylinder-like capsule.

In the case of pills or tablets, the bar code is preferably printed or engraved on the drug. As shown in FIGS. 1, 2, and 4, a typical drug pill or tablet has the shape of a disk 54. The diameter of such a pill is typically on the order of 4–10 mm. In a first embodiment of the invention, as shown in FIGS. 2 and 4, a radial bar code 60 may be used, which provides optimal data storage for a small radial surface such as a tablet. In an alternative embodiment, as shown in FIGS. 1 and 3, a miniaturized version of a conventional bar code, which uses thin parallel bars 53, may be used as the coding system. The width of bars 53 is preferably sufficiently small, even less than 0.1 mm, to enable sufficient identification information for the drug to be coded onto the surface of the tablet. If the tablet is sufficiently large, a conventional bar code may be attached thereto. As shown in FIGS. 3, 7, and 8, for drugs that are dispensed in capsules 52, a code, preferably a miniaturized conventional bar code, may be applied to the surface of the capsule.

The code, whether a bar code or a radial code, may be applied as bars painted on the pill during or after the manufacturing process, or may be applied to the tablet on a label 50. The paints applied to the pill and the colors on label 50, as well as the label itself, are made of bio-compatible materials.

In an alternative embodiment, the code may be applied to the tablet 54 or capsule 52 by applying two layers of different colors to the tablet or capsule. In this embodiment, the outer layer will have bar-like holes through which the inner layer will be exposed. In another alternative embodiment, in order to maximize the information that may be stored on a given tablet, a code using colored bars or bands may be used. Such a coding system is in use, for example, to code electrical resistors. Preferably, the colored bands extend coaxially around the drug capsule parallel to one another.

As shown in FIGS. 5, 6, 7, and 9, the bar code may also be applied by molding bars 57 on the surface of tablet 54, molding bands 64 coaxially around capsule 52 (FIG. 8), or by cutting away or etching the outer surface of the capsule or tablet to form the bars of bands, preferably during the manufacturing process. Paint or dyes may be added to the bars or to the materials from which the drug is made in order to enhance the visibility of bars 57. If desired, the entire outer surface of the tablet or capsule may be coated with a colored coating, and the bars may be formed by removing the coating using any conventionally known means.

Figure 12:
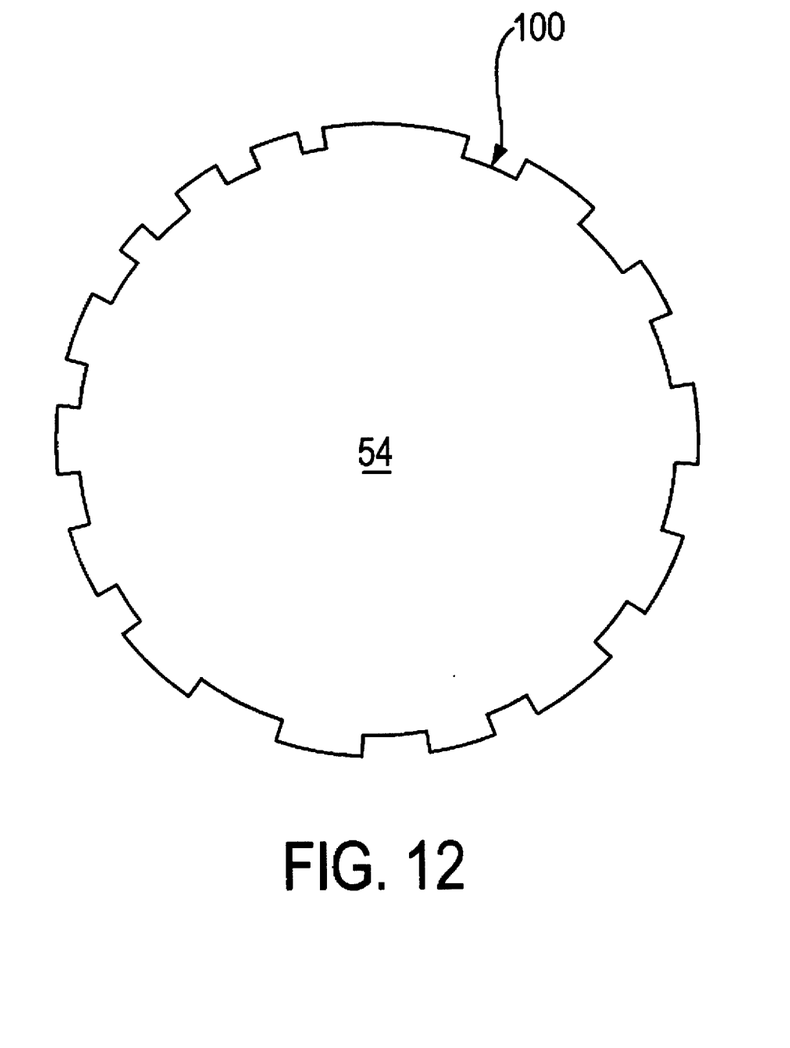
FIG. 12 is a schematic representation of a tablet with a corrugated periphery wherein the corrugation represents bars of different width and spacing.

In an alternative coding system, a bar code, which consists of indentations 100 or protrusions, may be engraved on the outer peripheral edge of tablet 54, as shown in FIG. 12. These indentations are similar to those often placed on coins, except that the spacing and width of the indentations would vary to provide a coding function. Using such a coding system, numerous bars may be engraved on a tablet, even those having small diameters.

Figure 10:
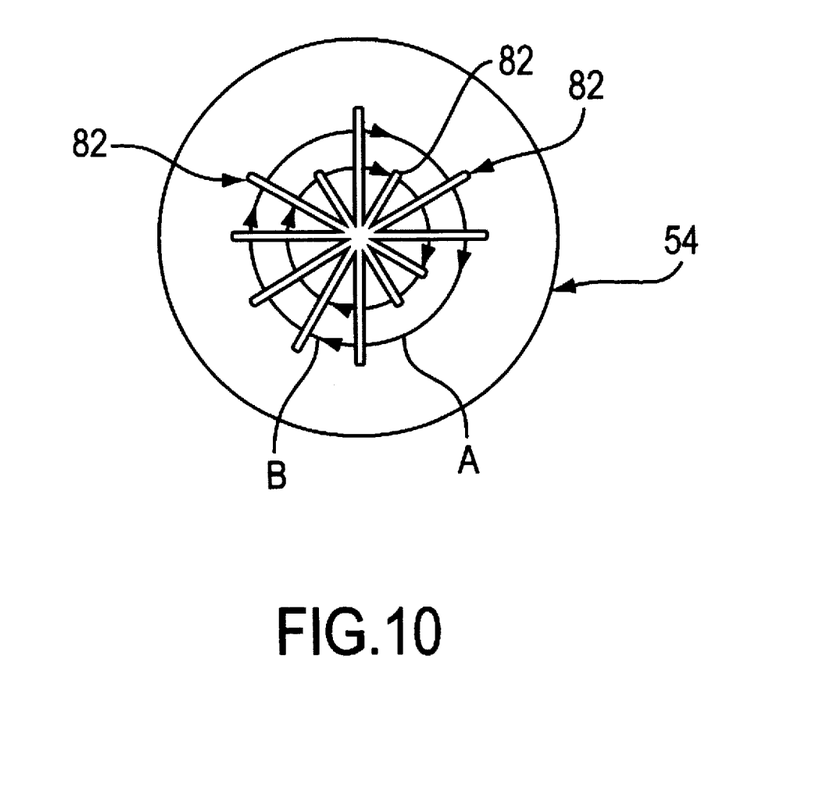
FIG. 10 is a schematic representation of a tablet with a radial bar code with bars of different lengths.

In another alternative method of coding tablets 54, as shown on FIG. 10, radial bars 82 may be employed which vary in angular spacing between bars, e.g., A and B, and in the length of the bars. Other applicable known methods of coding tablets include applying radial rings to the tablets as is done by the postal service (see, W. H. Erdei, *Bar Codes*, McGraw-Hill, New York, (1993); and T. V. Sobczak Ed., *Applying Industrial Bar Coding*, Soc. of Manuf. Eng., Dearborn, Mich., (1985)), applying labels to the tablets that include optically encoded data, as is done in optical compact disks, or holograms. In the case of optically encoded data, two layers of coating may be used, with the inner layer reflective and the outer layer opaque. The outer layer includes perforations that code the information. Since optical markings may be detected in the micron range, a large quantity of information may be stored even on very small surface tablets.

Whatever the coding system in use, each tablet or capsule is preferably coded to include the name or type of drug, and dosage of the drug. The code preferably includes checking characters, for example checksum characters, to minimize errors while reading the code.

Code Readers

The particular code reader for reading the coded pills will vary depending upon the type of code in use. There exist numerous types of coded information readers, each type being applicable to a particular type of code. Most code readers for reading bar codes of the type discussed above are optical code readers. Others types of readers exist for reading other types of codes, such as those for reading magnetically enciphered codes, RF codes, Surface Acoustic Wave codes, magnetic stripe codes, etc. These and other types of readers are described in more detail in the aforementioned book entitled *Bar Codes* and will not be discussed herein in further detail. It is foreseen that medication tablets and capsules may be coded using such other coding and reading systems, and that use of such other coding and reading systems to code medications is within the scope of the present invention.

Figure 11:
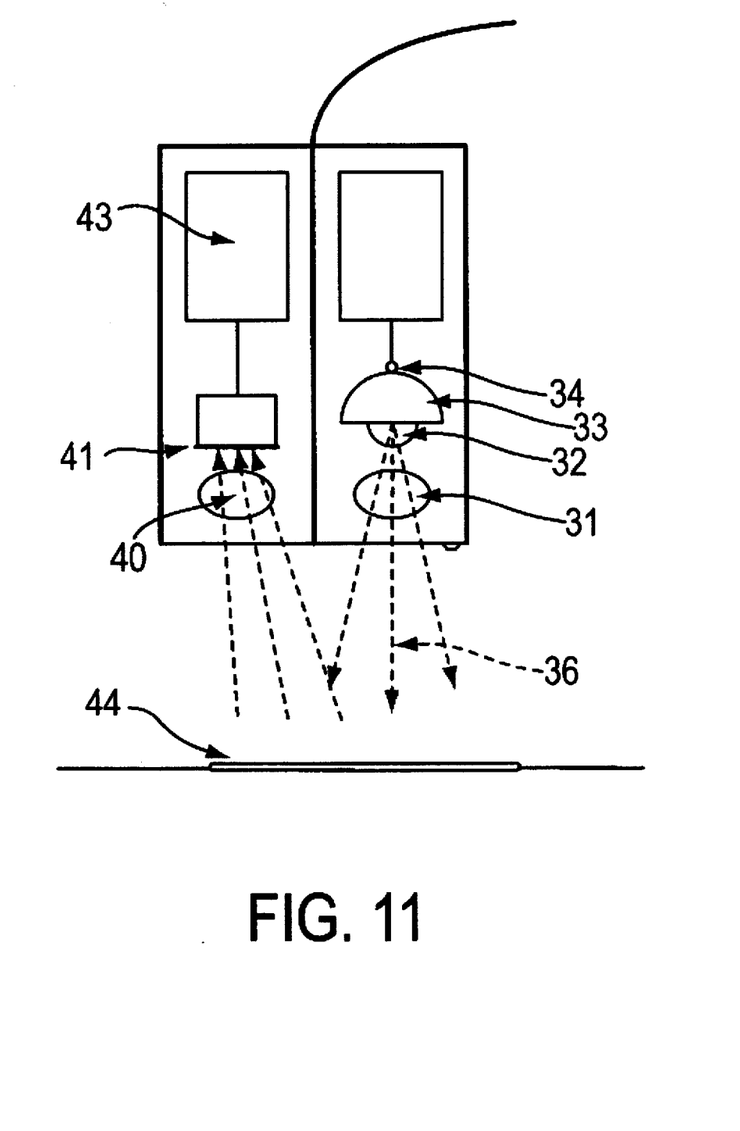
FIG. 11 is a schematic representation of the components and operation of a bar code reader.
Figure 13A:
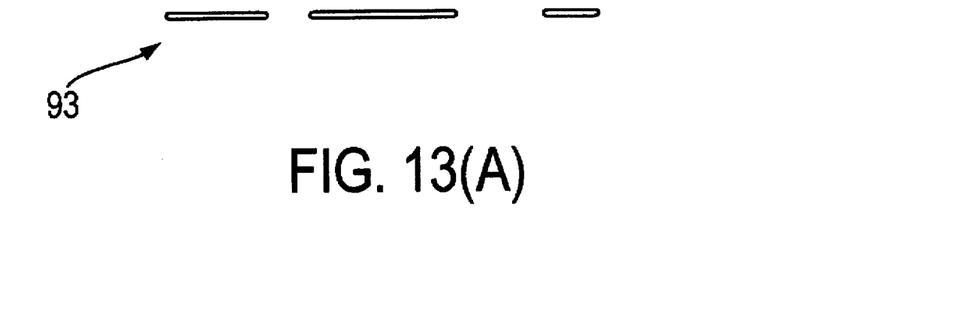
FIG. 13 is a schematic representation of the electric signal that corresponds to a bar code.
Figure 13B:
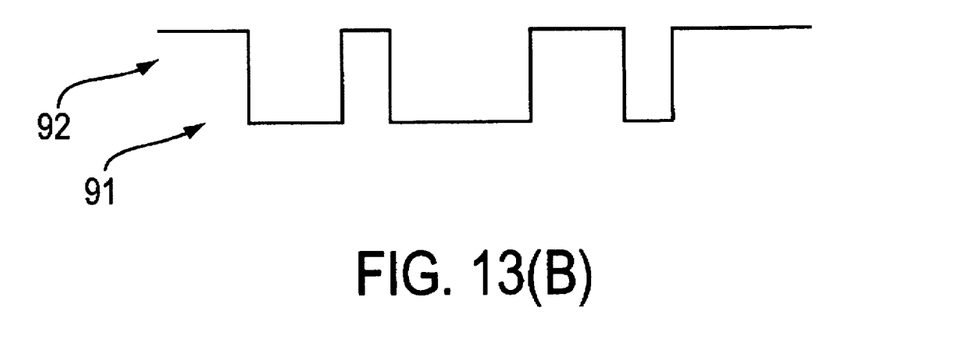

As illustrated in FIGS. 13A and 13B, a typical optical code reader converts the light and dark bars 93 of a conventional bar code into two levels of intensity 91 and 92 which are then converted to electrical signals so that they may be recognized and interpreted. As shown in FIG. 11, these readers typically scan the area where the coded information is registered with a laser beam 36. The scanning is typically achieved by a moving mirror, such as a reflector 33 that is rotated about a rotational axis 34. A light source 32 is preferably a laser or laser diode. An optical lens system 31 converts the light into a beam 36. The beam scans the code 44 and the reflected light passes through an optical lens system 40 which produces an image of the scanned area on photodetectors 41. The optical lens system is especially important for reading the very thin and small bar codes on tablets. The reflected light signal is converted by the photoelectric elements into electrical signals in a manner well known in the art. A detections system 43 then determines the width of the electrical signals which is used to translate the signals to numbers or characters in a well-known manner such as described in the aforementioned *Bar Codes* and *Applying Industrial Bar Coding*, and in H. E. Burke, *Automating Management Information Systems*, Vol. 1, Van Nostrand Reinhold, New York, (1990); and T. V. Sobczak, *Machine-Readable Marking Codes: Who Specifies What Type of Symbology?*, Computers and People, Feb. 1978.

Readers for the miniaturized and radial bar codes described above are generally similar to the conventional bar code reader described. When a radial bar code is used, as depicted in FIGS. 2 and 4, the scanning mechanism is preferably of the rotational type, rather than the linear type. When radial bars of two lengths are used, as shown in FIG. 10, the photoelectric system includes two or more readers, each corresponding in position to the lengths of the bars, to read the light emitted from the bars of different lengths.

If color coded bars or rings are in use, the light source is not a conventional laser beam but is instead a white light source, an incandescent lamp, a halogen lamp, etc. Color interpretation is made by using a series of light filters as is well known in the art.

Figures 5, 9:
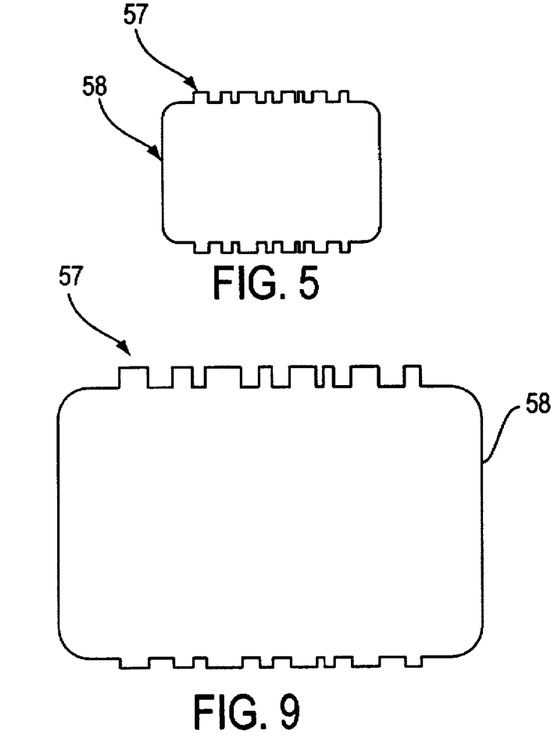
FIG. 5 is a schematic representation of the shadow cast by a tablet with engraved bars.
FIG. 9 is a schematic representation of the enlarged shadow cast by a tablet with engraved bars.

If the code is engraved on the surface of the tablet or capsule, as shown in FIGS. 6–8 and 12, the tablet or capsule is placed on a transparent surface with a light source positioned such that the light would cast a shadow 58 of the tablet on a surface. In shadow 58, the engraved code is seen as protrusions 57 from the main body of the shadow. A reader, which is positioned in direct view of the surface on which the shadow is projected, scans the shadow to detect the protrusions 57 based upon the two light levels of in the shadow, and converts these levels to corresponding electrical signals. In a preferred embodiment, the light source is fixed while a photodetecting element in the reader scans the image of the shadow. If desired, the shadow may be magnified, as shown in FIG. 9, during detection. Shadow detection may also be used to read codes on the outer peripheral edge of drugs, such as shown in FIG. 12.

Figure 14:
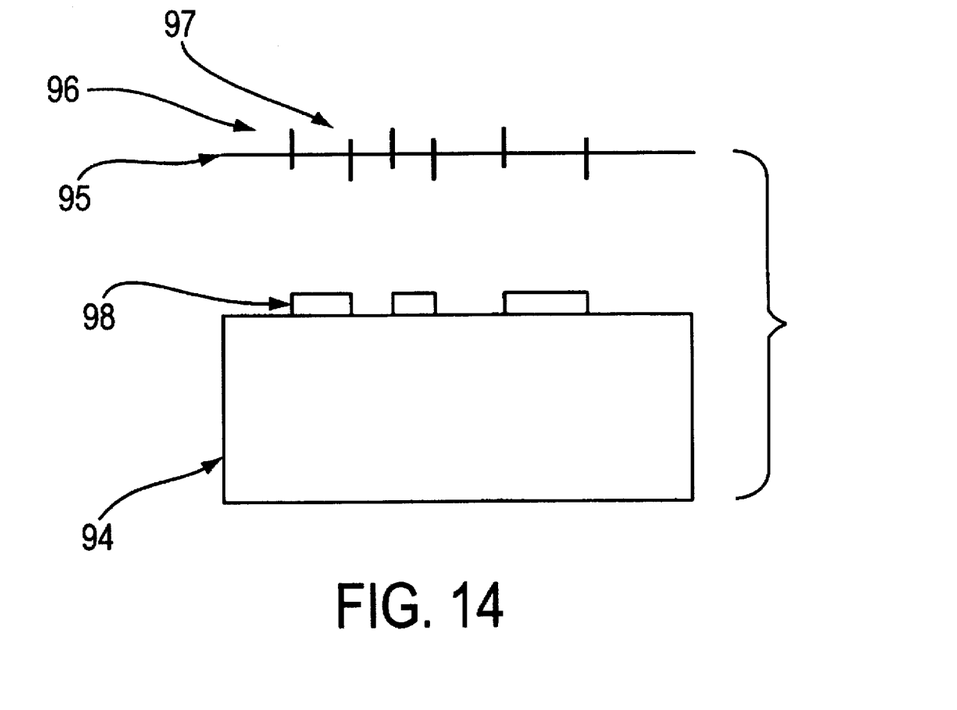
FIG. 14 is a schematic representation of the electric signal that corresponds to a tablet with an engraved bar code on its surface periphery.

In an alternative reader for reading engraved bar codes, a light beam scans the tablet surface, preferably in a linear pattern for codes of the type shown in FIGS. 6–8, and preferably in a circular scanning pattern for codes of the type shown in FIG. 12. As shown in FIG. 14, as long as the light is reflected from the non-engraved portion of the tablet or capsule, it has a constant intensity 95. When the scanning light beam hits the edge of a bar, e.g., 98, whether formed as an indentation in the surface of the tablet or capsule 94 or as a protrusion from the surface, the change in the height of the surface results in a transient light intensity change 96 that is detectable. As the light beam continues to scan the bar code, it again has a constant intensity. When it reaches the second edge of the engraving a second transient in light intensity 97 is detectable. The reader will detect the distance or time elapsed between transients as the width of a bar, or the distance between bars.

Alternatively, the reader may be positioned relative to the surface of the tablet, preferably at a relatively small angle, and scans the tablet so that light that falls on the disk surface will be reflected away from the reader, but light striking surfaces protruding or retracted from the plane of the tablet surface will be reflected back toward the reader so as to be detected.

Regardless of the type of reader in use, techniques for interpreting the light intensity changes to determine the content of the coded information is well known in the art.

At least two types of information are preferably encoded on the drug: A number or other information representative of the name of the drug; and, the dose, weight, number of activity units, etc. of the drug.

Each patient is also preferably identified by a conventional bar code or by any of the other codes discussed above. The patient code is preferably on a bracelet worn by the patient, on a label positioned on the patient's file or bed, or in any other appropriate location. When a standard bar code is used, a standard bar code reader may be used to read the patient code. When another type of coding is used for the patient code, an appropriate code reading device is used.

The code reader is preferably portable and contained on a cart so that it may be moved to a location at which a drug is to be dispensed, such as at the patient's bed. Power may be supplied to the reader by batteries or other well known means.

The Control System

The control system is preferably directly connected to the code reader, and is also preferably portable so that it may be moved with the code reader to the location at which drugs are delivered. The control system monitors the delivery of drugs to patients, and prevents the administration of the wrong drugs to patients.

The control system is preferably microprocessor controlled and includes an input/output device, such as a disk drive, or an RS/232 serial data bus for communicating with outside devices. Before a drug is to be distributed to a patient, the operator downloads to the controller from the hospital's central computer or from a local computer a file that contains patient names, medication delivery instructions, and medication delivery times for each patient. This download occurs by means of the means of the disk drive, RS/232 or other I/O device. The controller includes an appropriate memory device, such as a hard disk drive or RAM for storing the desired drug delivery file. As a nurse approaches each patient to whom drugs are to be delivered, the nurse uses the code reader to scan the bar code identifying the patient and the bar code identifying the drug to be delivered. The code reader decodes the identifying information on the patient and the drug and communicates this information to the controller which then looks up the patient file containing the desired drug delivery information for the patient.

The control system compares the drug, dosage, and time of delivery of the drug being delivered to those contained in the file for that patient. The control system will sound an alarm when a significant discrepancy exists between what drug a patient should receive and when it should be received. A display may be provided to indicate the nature of the discrepancy. The warning signal will also sound if, at the termination of drug delivery rounds, a patient did not receive his/her medication(s).

In addition, the control system may include a database of permissible drugs, doses etc. so that it may warn the nurse whenever a patient is about to receive an unusual or unacceptable drug or dosage, or combination thereof.

Coding Apparatus

Figure 15:
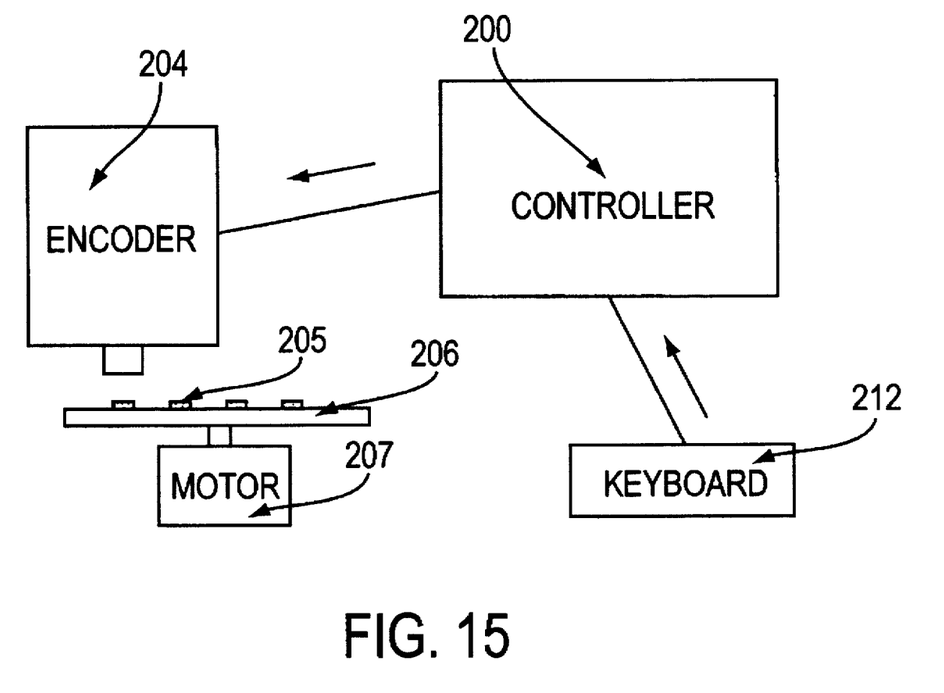
FIG. 15 is a schematic view of an encoding apparatus according to the present invention.

FIG. 15 shows an apparatus for coding individual drugs which may be used at the time the medication is manufactured or at the drug delivery site, e.g., a hospital pharmacy. A microprocessor-based controller 200, which may be a personal computer or a hospital computer system, contains a database of codes to identify individual drugs. The database will include a unique code identifier for each drug and dosage or procedure. A conventional menu driven display allows codes to be added to or deleted from the database by means of keyboard 212. Alternatively, provided that a uniform coding system exists, the database may be retrieved from a disk, LAN, or other I/O device.

An encoding apparatus 204 applies the appropriate code to medication 205. The medication 205 is preferably placed on a conveyor 206 that is operated by a conventional motor 207. Conveyor 207 passes the medication by a coding station at which the code is applied. Encoding apparatus 204 will vary depending upon the type of code to be applied. In one embodiment of the invention, encoding apparatus 204 prints and applies bar code labels to the medication passing on the conveyor. Systems for printing and applying coded labels are well known in the art. If desired, the labels may be pre-printed in a different facility and only applied by the encoder 204. If optically or magnetically encoded labels are used, these may also be printed elsewhere and loaded into encoding apparatus 204 to be applied to the medication. In any case, the label is constructed of a digestible material, such as dried gelatin or other materials that are used, for example, to coat pills or to construct edible capsules. The label is adhered to the medication with an edible, biocompatible adhesive. The conveyor aligns the medication to a desired position for the encoding process.

If the code is to be applied directly on the surface of the medication, rather than on a label, encoding apparatus may be any means known in the art for writing or painting on a surface, e.g., an ink-jet writer, a pin writer, a writer that uses masks to create the symbols, an ink roller, etc. The code is applied with only biocompatible edible inks and colors.

If the code is to be applied to the medication by engraving, encoding apparatus 204 may be any appropriate device for engraving the medication, i.e., a sharp pointed pin, a heated pin, a rotating bit, a pressurized stream of air or fluid, an ultrasonic etching device, etc. The movement of the engraving apparatus on the surface of the medication is controlled by the controller 200. The visibility of the engraved code may be enhanced by using colored layers such that the etching or engraving exposes a hidden layer that is of a different color, or by applying colors or dyes to the engraved surfaces.

In operation, the hospital pharmacist will use a computer interface on computer-controller 200 to select a drug and dosage to be encoded on particular medication. The medication will be placed on the conveyor and passed by encoding apparatus 204. Controller 200 will communicate the proper code to be applied to the medication to encoder 204 which will properly code the medication. The medication is then removed from the conveyor and administered using the procedure described above.

When the medication, fluid, paste, cream, etc. is packaged individually, the coding may be accomplished by applying a label directly to the packaging. With respect to medical procedures, e.g., X-rays, the technician will preferably have a pre-printed sheet of codes, with a code identifying the nature of each procedure. For example, the code sheet will have various codes for different body areas to be X-rayed, and codes for different durations and intensities of the X-rays. Before each person receives an X-ray, the technician scans the code for the body part, duration, and intensity of the X-ray to ensure that a patient has not been overexposed, for example. Similar coding schemes may be applied to other procedures, and cross-checking may be done to avoid dangerous combinations of procedures in the same manner that testing is done to prevent dangerous drug interactions.

Although the present invention has been described in detail with respect to certain embodiments and examples, variations and modifications exist which are within the scope of the invention as defined in the following claims.

I claim:

1. A method of delivering a drug pill to a patient, the method comprising:
   (a) placing a machine readable bar code on the outer surface of the pill, the code comprising identification information including the name and dosage form of the drug for insuring proper administration of the drug to the patient;
   (b) reading the bar code identification information from the pill with a code reader;
   (c) reading desired drug delivery information for the patient from a drug delivery information file with a code reader;
   (d) comparing the identification information on the pill with the desired drug delivery information;
   (e) generating an alarm upon detection of discrepancies between the pill identification information and the desired drug delivery information; and
   (f) delivering the drug pill to the patient in the absence of the generation of an alarm in accordance with step (e).

2. The method of claim 1 wherein the drug pill is a tablet.

3. The method of claim 2 wherein the machine readable bar code is located on an outer peripheral edge of the tablet.

4. The method of claim 1 wherein the drug pill is a capsule.

5. The method of claim 4 wherein the machine readable bar code extends completely around the capsule.

* * * * *